(12) United States Patent
Dellea et al.

(10) Patent No.: US 9,835,599 B2
(45) Date of Patent: Dec. 5, 2017

(54) METHOD FOR PRODUCING A CHROMATOGRAPHY ANALYSIS COLUMN

(71) Applicant: COMMISSARIAT A L'ENERGIE ATOMIQUE ET AUX ENERGIES ALTERNATIVES, Paris (FR)

(72) Inventors: Olivier Dellea, La Talaudiere (FR); Pascal Fugier, Bernin (FR); Helene Marie, Fontaine (FR); Severine Vignoud, Bernin (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 149 days.

(21) Appl. No.: 14/414,848

(22) PCT Filed: Jul. 2, 2013

(86) PCT No.: PCT/IB2013/055413
§ 371 (c)(1),
(2) Date: Jan. 14, 2015

(87) PCT Pub. No.: WO2014/013368
PCT Pub. Date: Jan. 23, 2014

(65) Prior Publication Data
US 2015/0219605 A1 Aug. 6, 2015

(30) Foreign Application Priority Data

Jul. 19, 2012 (FR) ..................... 12 57001

(51) Int. Cl.
*G01N 30/60* (2006.01)
*B01J 20/282* (2006.01)
(Continued)

(52) U.S. Cl.
CPC ....... *G01N 30/6052* (2013.01); *B01D 15/206* (2013.01); *B01D 53/025* (2013.01);
(Continued)

(58) Field of Classification Search
CPC .......... G01N 30/6052; G01N 30/6073; G01N 30/6095; B01D 53/025; B01D 15/206;
(Continued)

(56) References Cited

U.S. PATENT DOCUMENTS

| 6,887,384 B1* | 5/2005 | Frechet .................... B01J 20/26 210/198.2 |
| 7,727,314 B1* | 6/2010 | Manginell .............. G01N 1/405 422/88 |
| 2015/0233876 A1 | 8/2015 | Dellea et al. |

FOREIGN PATENT DOCUMENTS

| EP | 2048497 A1 | 4/2009 |
| FR | 2903679 A1 | 1/2008 |

(Continued)

OTHER PUBLICATIONS

Ji, Zhenghua et al., "Porous layer open-tubular capillary columns: preparations, applications and future directions", Journal of Chromatography, Elsevier Science Publishers B.V., NL, vol. 842, Nos. 1-2, May 21, 1999, pp. 115-142.*

(Continued)

*Primary Examiner* — Robert Clemente
(74) *Attorney, Agent, or Firm* — Arrigo, Lee & Guttman LLP

(57) ABSTRACT

The invention concerns a method for producing a chromatography analysis column, the resulting column, and a device comprising such a column. The method according to the invention comprises the following steps: (a) depositing on the flat surface of a substrate a first layer of particles which are intended to form the stationary phase; (b) depos-
(Continued)

iting on the layer at least one second layer of compactly assembled particles; (c) impregnating the first and second layers with a light radiation-sensitive material, to form at least two compactly assembled particle layers impregnated with sensitive material; (d) insolating these layers in the regions corresponding to the desired internal shape of the chromatography analysis column, if the light radiation-sensitive material behaves like a positive resin, or outlining this internal shape if the light radiation-sensitive material behaves like a negative photosensitive resin; (e) eliminating either the regions insolated in step (d) if the light radiation-sensitive layer behaves like a positive photosensitive resin, or the regions not insolated in step (d) if the light radiation-sensitive material behaves like a negative photosensitive resin; and (f) covering and sealing the structure obtained in step (e) with a cover covered on the face facing the layers with at least one layer of compactly assembled particles which are identical to or different from those deposited on the substrate surface. The invention is used in particular in the field of chemical analysis.

24 Claims, 3 Drawing Sheets

(51) Int. Cl.
B01D 15/20 (2006.01)
B01J 20/32 (2006.01)
B01D 53/02 (2006.01)
G01N 30/56 (2006.01)

(52) U.S. Cl.
CPC ......... *B01J 20/282* (2013.01); *B01J 20/3204* (2013.01); *B01J 20/3212* (2013.01); *B01J 20/3219* (2013.01); *B01J 20/3259* (2013.01); *B01J 20/3289* (2013.01); *G01N 30/6073* (2013.01); *G01N 30/6095* (2013.01); *B01J 2220/86* (2013.01); *G01N 30/56* (2013.01)

(58) Field of Classification Search
CPC .... B01J 20/282; B01J 20/285; B01J 20/3204; B01J 20/3206; B01J 20/3208; B01J 20/3212; B01J 20/3219; B01J 20/3259; B01J 20/3289; B01J 2220/86
See application file for complete search history.

(56) References Cited

FOREIGN PATENT DOCUMENTS

JP 2000002697 A * 1/2000
WO 2014/013370 A1 1/2014

OTHER PUBLICATIONS

Ji, Zhenghua, et al., "Porous layer open-tubular capillary columns: preparations, applications and future directions," Journal of Chromatography A, 842 (1999) 115-142.
Office Action, U.S. Appl. No. 14/414,853, dated Sep. 9, 2016.
Wei-Cheng Tian et al., "Multiple-Stage Microfabricted Preconcentrator-Focuser for Micro Gas Chromatography System," Journal of MIcroelectromechanical Systems, vol. 14, No. 3, pp. 498-506 (2005).

* cited by examiner

METHOD FOR PRODUCING A CHROMATOGRAPHY ANALYSIS COLUMN

The invention relates to a process for the manufacture of a chromatography analytical column, to a chromatography analytical column and to a device comprising such a chromatography analytical column.

The constraints brought about by increasingly strict regulations with regard to the safety of industrial plants (refineries, oil platforms, chemical plants, and the like), the need to monitor and watch over the quality of the air which we breath at our places of work or in our daily traveling involve the development of novel tools for the analysis of gases at odds with those available commercially in order to introduce substantial savings in terms of portability, sensitivity, selectivity, multiplicity of the identifiable analytes or cost.

In the field of in situ gas analysers, those available commercially do not meet all of these criteria, despite a great variety of technologies on the market (semiconductor: lack of selectivity, drift, influence of humidity; electrolytic: problem of recalibration; optical in the infrared region: size and cost, and the like).

For the analysis of complex gas mixtures, the reference method is Gas Chromatography (GC) coupled at the column outlet to a detector of TCD (thermal conductivity detector) or FID (flame ionization detector) type.

In order to complete the analyses, the chromatographs are often coupled to other analytical instruments, in particular mass spectrometry and infrared spectroscopy. However, these devices remain typical laboratory tools, bulky and very expensive. However, recent progress in micro- and nano-technologies open the way to the miniaturization of this type of high-performance and universal analyser.

The gas phase chromatography (GPC) technique is one of the most widely used separation and analytical methods for volatile or semi-volatile compounds. In particular, in combination with mass spectrometry, it is the method of choice for the analysis of complex gas mixtures in many fields: environment, safety, pharmaceutical industry, food processing industry, petrochemicals, and the like.

The commonest current equipments are difficult to transport and are expensive. An advantageous route to miniaturization involves the production of microcolumns etched into silicon. Apart from the advantage of the basic reduction in size, micromanufacture on silicon makes it possible to envisage novel forms of microcolumns, the monolithic incorporation of several columns and/or of other functional elements (injector, detector) on the same chip, and also mass production, eventually making possible a large reduction in the costs.

The separation efficiency of the microcolumns is based on the difference in affinity of the analytes with the "stationary" phase (layer deposited on the wall of the channels) and the "mobile" phase (the carrier gas) and thus on the differential migration obtained for these analytes.

A good separating power characterizing a high-performance column involves a deposited layer which is homogeneous in composition and thickness over all the walls of the column. The deposition processes used today for silicon columns are very similar to those used for capillary columns.

Even if the obtained separation efficiencies are of the same order of magnitude as in a standard column, these processes remain chip by chip processes, that is to say processes in which the components are treated one after the other, and are limited by the non-homogeneity of the depositions, with, for example, excess thicknesses of the layers of materials deposited in the corners of the channels. There is plenty of room for progress, both at the performance level and at the level of reduction in the manufacturing cost, by the development of specially suited processes.

Furthermore, it has been shown that columns of PLOT (Porous Layer Open Tubular) type, exhibiting a structured internal surface having a high surface to volume ratio, are more effective for the separation of certain mixtures, in particular permanent gases and light alkanes, essential compounds of natural gas and biogases.

These columns are chromatography analytical columns, in contrast to chromatography-enrichment columns, which for their part are used to concentrate the mobile phase in analyte to be detected and/or analysed, before it is passed through the analytical column proper.

The columns of PLOT type are hollow columns comprising a layer of porous stationary phase deposited on the internal wall of the column.

They form a hollow tube, that is to say that the stationary phase or porous layer does not completely fill the column.

In silicon technology, that is to say when the wall of the microcolumns is composed of silicon, the stationary phase is deposited similarly to the PLOT columns but the deposited layer obtained exhibits a non-homogeneity prejudicial to the detection.

This non-homogeneity is due to the geometry of the channel, the cross-section of which is parallelepipedal or trapezoidal: there is thus an excess thickness of the stationary phase at certain points of the column, in particular in the angles.

Provision has thus been made to deposit particles as a compact assemblage in the channel and on the sealing covering cap. This route is described in FIG. 1.

As seen in FIG. 1, a silicon substrate, denoted 1a in FIG. 1, is etched, in order to form the desired internal shape of the column, and then the surface of the substrate 1a in which this shape has been formed is activated, for example by plasma, by treatment with UV radiation or by a "piranha" solution. A piranha solution is a solution composed of sulfuric acid and of hydrogen peroxide.

The particles intended to form the stationary phase, denoted 2a in FIG. 1, are then deposited on the activated surface of the substrate 1a. The activation of the surface of this substrate 1a makes it possible to create strong covalent or hydrogen bonds between the activated surface of the substrate 1a and the particles 2a.

Finally, a covering cap, denoted 7a in FIG. 1, itself also comprising a layer, denoted 8a in FIG. 1, of particles of the stationary phase, is sealed over the substrate obtained in order to close the column.

The covering cap, denoted 7a in FIG. 1, is fitted so that its surface covered with particles 8a faces the surfaces also covered with particles 2a of the substrate 1a.

The sealing can be obtained, for example, by deposition of an adhesive, denoted 9a in FIG. 1, on the edges of the substrate 1a, as shown in FIG. 1.

However, by this process, the deposition of the film of particles on the vertical walls is difficult. This is because the geometric configuration of the channel makes it difficult to produce a deposition of particles as a conformable compact assemblage, that is to say one which follows the shape of the walls. Whatever the deposition technique employed, there will be shortages of particles on the vertical walls and thus non-homogeneities in the stationary phase.

The invention is targeted at overcoming the disadvantages of the processes of the prior art by providing a process which can be applied to any type of substrate and which does not require the etching of this substrate. By this method, low-cost components on plastic can be envisaged.

The process of the invention makes it possible to have particles homogeneously distributed over all the internal phases of the column. It makes it possible to construct the stationary phase layer by layer and thus to combine particles having different natures, dimensions and/or surface activations.

Furthermore, as the substrate is not etched, the great majority of the techniques for deposition of particles as a compact assemblage are compatible in carrying out the deposition of the particles. In the case of an etched substrate, techniques such as the spin technique cannot be employed because of the surface topology related to the etchings.

Thus, the invention provides a process for the manufacture of a chromatography analytical column, characterized in that it comprises the following steps:

a) deposition of a first layer of particles, which are intended to form the stationary phase, on the flat surface of a substrate, b) deposition of at least one second layer of particles as a compact assemblage on the layer, c) impregnation of the first and second layers with a material sensitive to light radiation, in order to form at least two layers of particles as a compact assemblage impregnated with sensitive material, d) insolation of these layers in the regions corresponding to the internal shape desired for the chromatography analytical column, when the material sensitive to light radiation behaves as a positive resin, or outlining this internal shape, when the material sensitive to light radiation behaves as a negative photosensitive resin, e) removal:
  of the regions insolated in step d), when the material sensitive to light radiation behaves as a positive photosensitive resin, or
  of the regions not insolated in step d), when the material sensitive to light radiation behaves as a negative photosensitive resin, and f) covering and sealing the structure obtained in step e) with a covering cap covered, on its face turned towards the layers, with at least one layer of particles as a compact assemblage identical to or different from those deposited on the surface of the substrate.

Preferably, the process of the invention additionally comprises, before step a), a step a1) of activation of said surface of the substrate. Preferably, this activation step is carried out by $O_2$ plasma, UV radiation or a mixture of sulfuric acid and of hydrogen peroxide.

In this case, preferably, the process of the invention also comprises, after step a1) itself, a step a2) of anchoring, to the surface of the substrate, particles of said first layer. This step a2) can be a step of thermal annealing or also a step of impregnation of this first layer with a photosensitive resin, followed by an insolation of this photosensitive resin with the light radiation appropriate for crosslinking this resin.

Preferably again, the process of the invention additionally comprises, after step b), a step b1) of heat treatment of the layers of particles impregnated with sensitive material obtained in step b), in order to stabilize this sensitive material and to remove the residual solvents.

Preferably also, the process of the invention comprises, after step c), a step c1) of thermal annealing in order to finalize the crosslinking of the regions of insolated sensitive material.

Still preferably, the process of the invention additionally comprises, after step d), a step d1) of heat treatment of the layers obtained in step d), preferably at a temperature of between 50° C. and 170° C. inclusive, for from 1 to 10 min inclusive.

Preferably also, the process of the invention additionally comprises a step of formation of at least one layer of particles as a compact assemblage on a face of a covering cap.

Preferably again, the particles used in the process of the invention have a mean diameter, measured by a Zetasizer®, Nanosizer® or scanning electron microscope, of between 50 nm and 500 µm inclusive.

Preferably again, the total thickness of the layers formed on the substrate is between 50 and 700 µm inclusive.

The particles which can be used are particles made of a metal oxide, of polymer, of ceramic, of metal or of polysaccharide. They are preferably made of a material chosen from silica, titanium dioxide, alumina, latex, polydimethylsiloxane (PDMS), gold, copper and the mixtures of these.

The particles used in the invention are optionally functionalized.

Step a) can be carried out, for example, by the Langmuir-Blodgett method, or by the Langmuir-Schaefer method, or by Marangoni self-assembling, or by the vortical surface method, or by floating-transferring, or by dip coating, or by spin coating.

In a first embodiment of the process of the invention, the material sensitive to light radiation behaves as a positive resin sensitive to radiation with wavelengths of between 150 and 700 nm.

In a second embodiment of the process of the invention, the material sensitive to light radiation behaves as a negative resin sensitive to radiation with wavelengths of between 150 and 700 nm.

In a third embodiment of the process of the invention, the material sensitive to light radiation is obtained by a sol-gel process.

With regard to step c), it can be carried out by spin deposition of the material sensitive to light radiation on the layers of particles or by immersion of the substrate coated with the layers of particles in the material sensitive to light radiation. It can also be carried out by spraying or drop coating the sensitive material on the substrate coated with the layers of particles.

Step d) of insolation of the impregnated layer with light radiation can be carried out through a mask comprising regions transparent to said light radiation, these transparent regions corresponding to:
  the internal shape desired for the chromatography column, when the material sensitive to light radiation behaves as a positive resin, or
  outlining this internal shape, when the material sensitive to light radiation behaves as a negative resin.

However, step c) of insolation of the impregnated layer can also be carried out by laser writing in order to form the internal shape desired for the column, when the material sensitive to light radiation behaves as a positive resin, or in the regions outlining this internal shape, when the material sensitive to light radiation behaves as a negative resin.

Finally, preferably, in the process of the invention, the substrate is flexible or rigid and is made of a metal oxide, of a metal, of a ceramic or of a polymer. Preferably, the substrate is made of silicon.

The invention also provides a chromatography analytical column, characterized in that it comprises a substrate, a flat surface of which is coated with at least one layer of particles, this layer of particles, which are optionally functionalized, comprising a region devoid of the particles and forming the internal portion of the column and in that at least one wall of the column consists of a mixture of said particles, which are optionally functionalized, and of a material sensitive to light radiation, which is crosslinked.

Preferably, in the chromatography analytical column of the invention, the particles are particles made of a metal oxide, of a ceramic, of a polymer, of a polysaccharide or of a metal. Preferably, use will be made of particles made of titanium dioxide, of alumina, of silica, of polydimethylsiloxane, of latex, of gold, of copper or of a mixture of these.

Still preferably, the particles used in the invention are functionalized particles.

Preferably, these particles have a mean diameter of between 50 nm and 500 µm inclusive.

With regard to the substrate of the column of the invention, it can be flexible or rigid. It can be made of a material chosen from a metal oxide, a metal, a polymer or a ceramic. Preferably, the chromatography column of the invention is made of silicon.

The invention also provides a device, characterized in that it comprises a chromatography analytical column obtained by the process for the manufacture of a chromatography analytical column of the invention or comprises a chromatography analytical column according to the invention.

A better understanding of the invention will be obtained and other characteristics and advantages of the latter will become more clearly apparent on reading the explanatory description which follows and which is made with reference to FIG. 2, which shows, in diagrammatic fashion, the various steps of the process of the invention.

Overall, the process for the manufacture of a chromatography analytical column according to the invention consists in depositing, at the surface of a substrate, denoted 1 in FIG. 2, which is unstructured, that is to say the surface of which is flat, a first layer, denoted 2 in FIG. 2, of particles intended to form the stationary phase as a compact assemblage (also known as colloidal crystal) over a thickness sufficient to form microcolumns.

The substrate 1 can be flexible or rigid and can be made of a metal oxide, of a metal, such as silicon, of a polymer or of a ceramic. When the substrate has to be flexible, it will preferably be made of a polymer, such as poly(ethylene terephthalate) (PET), poly(ethylene naphthalate) (PEN) or a polycarbonate (PC).

With regard to the particles, they can be made of a metal oxide, of a metal, of a polymer, of a polysaccharide or of a ceramic. Preferably, these will be particles made of a material chosen from silica, alumina, titanium dioxide, latex, polydimethylsiloxane (PDMS), gold, copper and mixtures of these.

These particles can be optionally functionalized. The particles can all be functionalized but only some of them can be functionalized.

This shows the great flexibility of the process of the invention and the great variety of stationary phases of chromatography analytical microcolumns which can be tailor-made.

At least one second layer, denoted 12 in FIG. 2, which is identical to or different from that constituting the first layer 2, is subsequently deposited on the first layer 2. The particles of the layers 2 and 12 also form particles as a compact assemblage.

Photolithography steps are then carried out in order to create the microchannels of the microcolumn.

Depending on the bi- or multilayer structure to be insolated, the insolation is carried out under a mask or with a laser appliance specifically designed for the insolation of photosensitive materials deposited as thick layers, that is to say with a thickness from 10 up to 500 µm inclusive.

In order to finish, a step of sealing the microcolumn is carried out.

More specifically, in order to obtain a hollow channel of the microcolumn type, the process of the invention comprises the following steps: deposition of a first layer 2 of particles as a compact assemblage on the surface of a substrate 1, deposition of at least one second layer 12 of particles identical to or different from that of the layer 1, also as a compact assemblage, on the layer 2. Impregnation of the layers 2, 12 with a photosensitive material. In the case represented in FIG. 2, the photosensitive material behaves as a positive resin. A stack of layers of microparticles impregnated with photosensitive material, which are denoted 3 in FIG. 2, is then obtained.

Preferably, a thermal annealing operation is then carried out in order to stabilize the stack of microparticles which are impregnated with photosensitive materials. However, this step is not an essential step but simply a preferred step of the process of the invention.

These layers 3 are then insolated through a mask, denoted 11 in FIG. 2, comprising regions transparent to light radiation, denoted 4 in FIG. 2, to which the photosensitive material is sensitive, these transparent regions having the shape of the internal cavity of the microcolumn to be manufactured.

The photosensitive material can also be insolated by laser writing in the desired regions of resin in order to form the internal shape of the microcolumn, in which case a mask is not used.

The sensitive material is then developed, that is to say that the non-insolated portion of the stack of layers 3 is removed, in the case of a photosensitive material behaving as a positive resin, as shown in FIG. 2.

Sealing is then carried out, for example by bonding with a covering cap, denoted 7 in FIG. 2, having a layer, denoted 8 in FIG. 2, of particles of stationary phase deposited at the surface.

Here again, these particles can be identical to or different from those constituting the layers 2 and 12.

It will also be possible to use a photosensitive material behaving as a negative resin, in which case the regions outlining the internal shape desired for the column to be obtained will be insolated, either through a mask comprising transparent regions outlining the internal shape desired for the column to be obtained or by laser writing.

Thus, as seen in FIG. 2, the column according to the invention is composed of a substrate 1, a flat surface of which is covered with at least two layers 3 of particles, these layers 3 comprising a region, denoted 5 in FIG. 2, in which there are no microparticles. However, as seen in FIG. 2, the surface of the substrate still comprises at least one layer, denoted 10 in FIG. 2, of particles.

The particles forming the layers 3 are identical to those already described, with reference to the process for the manufacture of a microcolumn of the invention.

They can be functionalized with molecules, for example molecules specific and selective for the compound to be detected in the mobile phase. This functionalization can be carried out by grafting or adsorption of said specific and selective molecules. It should be emphasized that it is necessary to preserve the whole or a significant portion of the active functional groups (microchannels) of the chromatography analytical microcolumn of the invention making possible the adsorption of the gases or fluids.

Furthermore, the functionalized particles have to be compatible with the photosensitive material (material sensitive to light radiation 4) making possible the production of the component.

In order to promote the deposition of the particles on the surface of the substrate and in order to make it possible to retain at least the first layer 2 of particles, the process of the invention preferably comprises a step of pretreatment of the surface of the substrate 1 before the deposition of the first layer 2 of particles.

This step is known as activation step. It can be carried out by $O_2$ plasma, by UV radiation, by treatment with a piranha solution (mixture of $H_2SO_4$ and $H_2O_2$) or by ozone. This activation treatment makes it possible both to remove possible organic materials physically absorbed on the substrate and to generate, at the surfaces, hydroxyl groups in order to obtain fixing of the particles intended to form the stationary phase. The hydroxyl groups can be silanol groups when the substrate is made of silicon. The deposition of the layers 2 and 12 of particles can be carried out by stacking the layers one after the other or directly and collectively. The mean diameter of the particles used is typically of 50 nm and 500 µm inclusive. In the invention, the mean diameter of the particles is determined by a Zetasizer®, Nanosizer® or scanning electron microscope. The thickness of the stack of the layers 2, 12 or 3 must make it possible to obtain a region of circulation of the mobile phase of 50 to 700 µm in the direction normal to the substrate. It is thus preferably between 50 and 700 µm inclusive.

The techniques which make it possible to produce a monolayer of particles as a compact assemblage are, for example:

The Langmuir-Blodgett method: This technique comprises a carrier liquid (for example water) in which the "target" substrate onto which the monolayer of particles has to be transferred is immersed beforehand in the vertical position. The particles are distributed at the surface of the liquid, over which they disperse. A mechanical device (known as barrier) is then set in motion in order to gradually reduce the surface area occupied by the particles in order to compress them. When the compact film is formed, the substrate is set in motion in order to deposit the film at its surface by capillary action. The barrier has to accompany this drawing movement in order to keep the particles compressed [1,2].

The Langmuir-Schaefer method: The principle of the Langmuir-Schaefer technique is basically the same as that used in the Langmuir-Blodgett case, the only difference being that the substrate is positioned horizontally [1].

Self-assembling by the Marangoni mechanism: The method of self-assembling by the Marangoni mechanism [3,4] is similar to those presented above. Specifically, while the deposition step is basically identical to the Langmuir-Blodgett method, the mode of assembling the particles is different: the particles, rendered hydrophobic, are dissolved in ethanol and dispersed at the surface of the water. The difference in surface tension between the ethanol (22 dyn/cm) and the water (73 dyn/cm) creates a surface flow, known as Marangoni flow, which results in a variation in the thickness of the ethanol film at the surface of the water. The agitation brought about by this phenomenon makes possible the organization of the particles among themselves.

The vortical surface method: The vortical surface method [5] consists in creating a vortex (using a magnetic stirrer) at the surface of the water and in dispersing the hydrophobic particles over this vortex. As the particles are hydrophobic, they remain at the surface of the vortex. Thus, the particles become organized among themselves by virtue of compression. The deposition on a substrate is carried out according to the Langmuir-Blodgett method.

Floating-transferring: The substrate is immersed beforehand in the liquid and the particles of polystyrene are deposited at the surface of the water; the particles are subsequently coagulated by addition of sodium dodecyl sulfate and the film is deposited by withdrawing the substrate from the water [6,7].

Dip coating.

Spin coating.

Spray coating.

The drop coating technique can be used to directly produce the multilayer structure [8,9]: a colloidal solution is deposited at the surface of the hydrophilic substrate and the slow evaporation of the solvent results in an ordered structure of particles. This technique is difficult to control over large surface areas and, in the case where particles of different natures or functionalizations are used it does not make it possible to control the composition of the layers forming the multilayer structure.

Photolithography is a conventional process widely used in microelectronics to manufacture micron-scale systems. The steps of the photolithography process begin by the application of a photosensitive material and the formation of a thin layer on the surface of a substrate (silicon, polymers, and the like).

The photosensitive material can be deposited in several ways.

After a thermal annealing, this layer impregnated with photosensitive material is subsequently exposed, partially, to light radiation. During this second step of the process, the use of a mask, composed of regions opaque and transparent to light radiation, makes it possible to define the geometric pattern which it is desired to reproduce on the substrate.

The principle of photolithography is based on the ability of photosensitive materials to experience a change in their solubility as a function of the amount of light radiation absorbed.

Several photosensitive materials can be envisaged and have to be selected according to their compatibilities with the functionalized particles: whatever the material used, it has to be neutral with respect to the functionalization of the particles, which functionalization has been carried out in order to detect the desired analyte, either of the same family or composition as a functionalization carried out on the particles or to introduce an additional element.

The materials which can be envisaged are:

Resins:
  positive resins, the illuminated portion of which is removed during the development, subsequent to the decomposition (photolysis) of the photosensitive portion of the photoactive compound (for example, DiazoNaphthoQuinone DNQ) which they comprise, and
  negative resins, which, on the contrary, crosslink under the effect of the radiation and the illuminated portions of which will be insoluble in the solvents used during the development.

Sol-gels, which can behave as positive resins or as negative resins according to the materials of which they are composed.

The principle of the sol-gel process, sometimes known as "mild chemistry", is based on the use of a sequence of hydrolysis-condensation reactions, at moderate temperature, in order to prepare networks of oxides which can, in their turn, be heat treated.

Organic-inorganic sol-gel hybrids make it possible to obtain chemically homogenous microstructures. The syntheses of organic-inorganic hybrid materials are widely described in the literature. Use may be made, for example, of sol-gels based on MAPTMS (MethAcryloyloxyPropylTriMethoxySilane) and on ZPO (Zirconium PropOxyde). A photoinitiator (such as Irgacure® 369 or 189 from CIBA) added to the solution confers, on this hybrid, the photosensitive properties of a negative resin and the variation in the concentration of ZPO makes it possible to vary the refractive index between 1.48 and 1.52.

The scheme presented in FIG. 3 illustrates the principal of the preparation of the sol-gel hybrid [2,10].

The final material comprises an inorganic network and an organic network. The inorganic network is obtained by hydrolysis and polycondensation of the alkoxide groups, while the organic network is created by polymerization of the double bonds, mainly C=C double bonds, under the action of the ultraviolet photons.

This network is represented diagrammatically in FIG. 4.

Generally, the photosensitive materials are spread over the substrate by spin coating. This process can be envisaged but there is a high risk of weakening the multilayer structure. Another solution consists in impregnating the structure by slowly and gradually immersing the substrate. The impregnation material fills the interstices between the particles via capillary forces.

In order to initiate the crosslinking reaction, the photosensitive material has to undergo exposure to light, preferably UV light. In this approach, the layer to be insolated is regarded by a person skilled in the art as thick (>10 μm). Appliances are currently on sale which make it possible to insolate such thicknesses by using the masking technique (for example: Q7000 mask Aligner®, supplier Neutronix-Quintel) or by writing by direct laser writing (for example: DILASE® appliance, supplier Kloé). The irradiation dose is adjusted as a function of the thickness of the film. It is the product of their radiation time and of the intensity of the light, preferably UV light.

The insolated photosensitive material is subsequently developed in order to reveal the microstructures. This phase is based on the dissolution of the photosensitive materials in a good solvent or successive rinsing operations with butanol and isopropanol for the sol-gel hybrids.

Several methods exist for the development of the resins. The commonest is immersion with stirring of the bath but evaporation may also be encountered.

The developer and the development process must not inhibit the functionalization of the particles making possible the separation of the gases and fluids.

An annealing for densification and relaxation of the stresses can also be carried out. It consists of a heat treatment. This heat treatment will not necessarily be carried out. However, it makes it possible to activate the end of crosslinking of the polymer network. Furthermore, when heat stresses and cracks appear after the development, this annealing makes it possible to relax the stresses and to stabilize the final structure.

With regard to the sealing of the column, generally, the industrial sealing of the microstructures is carried out according to different routes:

Liquid Route:

SiPix Imaging Inc. has developed several novel methods [12,13] for closing the microcups used in electrophoretic screens, all based on the principle of immiscibility between two liquids.

Solid Route:

Pressure-sensitive adhesives (PSAs) are elastomeric viscoelastic materials which can adhere strongly to a solid surface on applying a low pressure and a low contact time. The incorporation of oligomers sensitive to UV radiation and of photoinitiators in the formulation of the adhesives makes it possible to obtain UV-crosslinkable PSA adhesives [14]. With regard to hot-melt adhesives, they are deposited in the molten state (low viscosity) and their cohesion is provided during the cooling.

The covering cap, denoted 7 in FIG. 2, used for this sealing is a covering cap covered over its sealed face with a layer of particles 8 which are identical to or different from that constituting the layer 3.

By virtue of the process of the invention, the "edge" effects in particular are suppressed.

The chromatography analytical column thus obtained comprises at least one longitudinal wall composed of particles of stationary phase which are optionally functionalized and which are impregnated with a crosslinked material photosensitive to light radiation, as seen in FIG. 2.

In order for the invention to be better understood, two embodiments thereof will be described, as purely illustrative and nonlimiting examples.

EXAMPLE

Figure 1:
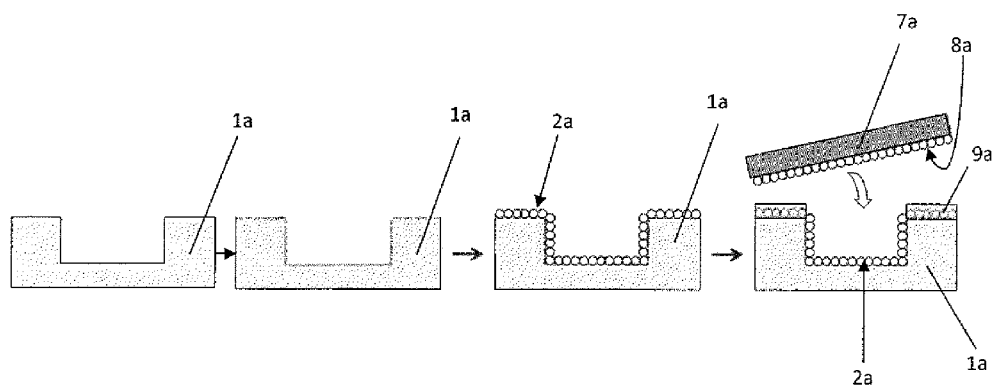
FIG. 1 shows depositing of particles as a compact assemblage in a channel and on a sealing covering cap.
Figure 2:
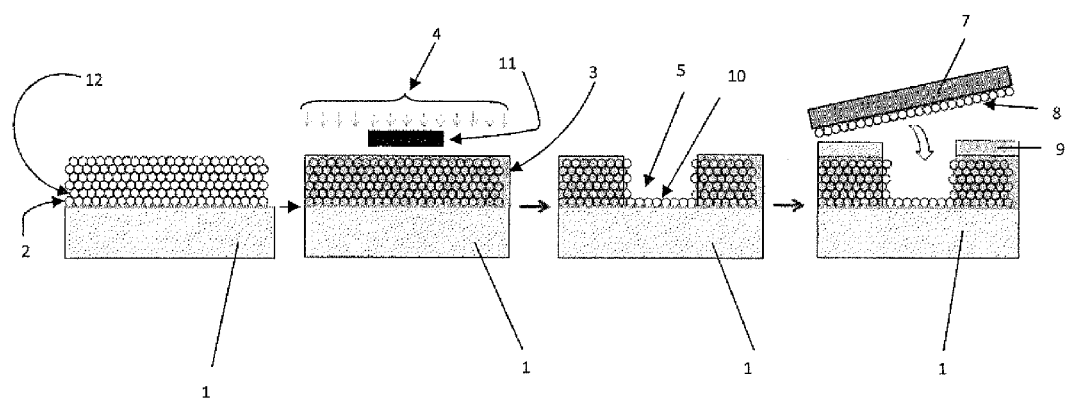
FIG. 2 shows the process for the manufacture of a chromatography analytical column according to the invention.
Figure 3:
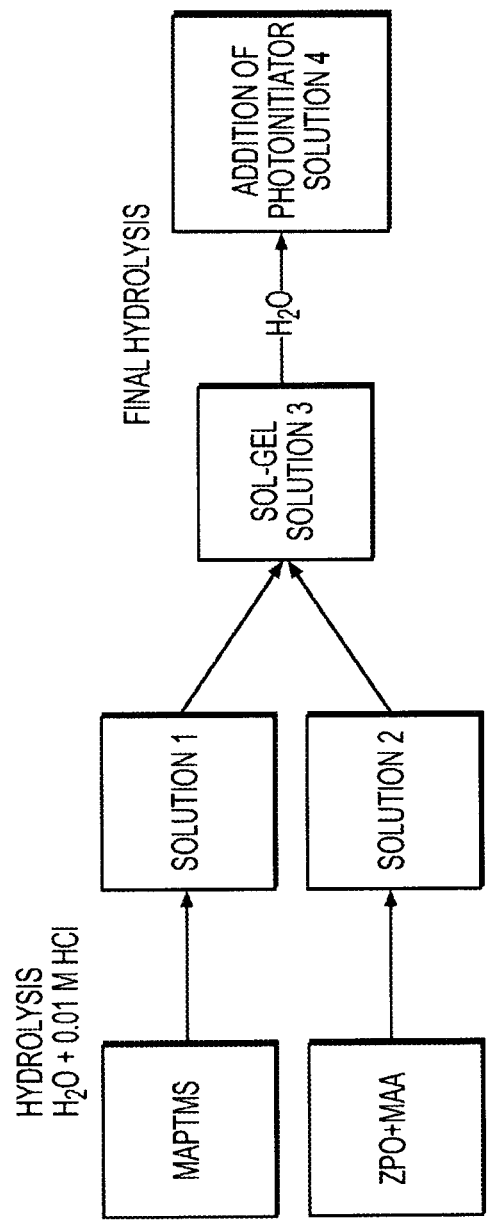
FIG. 3 illustrates the principal of the preparation of the sol-gel hybrid.
Figure 4:
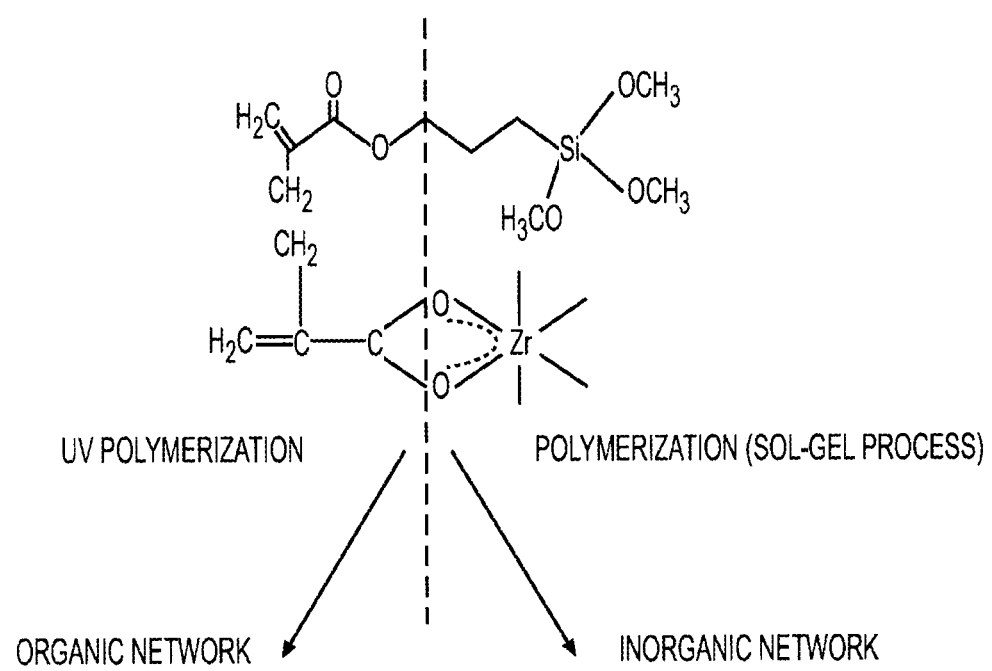
FIG. 4 presents a diagrammatical representation of an inorganic network and an organic network.

Example 1 a silicon substrate having a diameter of 7.62 cm (3 inches) comprising a layer of silica with a thickness of 100 nm obtained by thermal growth was subjected to a step a1) of activation of the surface by Brown treatment, that is to say dipping in a 0.1N sodium hydroxide bath.

Silica particles with a diameter of 1 μm functionalized by dipping with 5 mM 5,6-epoxyhexyltriethoxysilane in toluene at 80° C. for 16 hours, followed by rinsing with distilled water and drying at 110° C. for 3 hours, were deposited by the Langmuir-Blodgett method. A heat treatment at 110° C. for 3 hours was carried out on the substrate coated with the first layer of particles.

Due to the activation of the substrate, which comprises OH bonds, the first layer of particles functionalized with 5,6-epoxyhexyltriethoxysilane created covalent bonds between the particles and the substrate. In order to fix this first layer to the substrate, a heat treatment at 110° C. for 3 hours was carried out.

50 layers of the same particles as above were deposited by the Langmuir-Blodgett method at a draw rate of 1 cm/min.

The stack of layers was then impregnated with a positive photosensitive resin TELR-P0003PM, sold by TOK Europe (Tokyo Ohka Kogyo Co. Ltd), by spin deposition at 1000 rpm for 1 min.

The stack of layers was stabilized by thermal annealing at 110° C. for 2 min.

The combination obtained was then insolated by UV radiation with a wavelength of 365 nm, at 200 MJ/cm$^2$ for 15 seconds.

The resin was subsequently developed, that is to say that the regions of insolated resin were removed by immersion in TMA 238 WA, sold by JSR. The TMA comprises tetramethylammonium hydroxide. The immersion lasted a few seconds. The substrate coated with the layers was subsequently rinsed with water. The insolation was carried out by virtue of an MA750 laser appliance emitting wavelengths of 365 nm.

The substrate coated with layers of particles comprising, as a hollow, the shape of the desired microcolumn was heat treated at 110° C. for 1 h.

A covering cap coated on one of its faces with a layer of the same particles as described above was sealed by virtue of an adhesive at 110° C. for 30 min and then 160° C. for 1 hour under vacuum.

Example 2

In this example, the sealing covering cap was covered with particles by the following process:

A silicon substrate with a diameter of 7.62 cm (3 inches) coated with a layer of 100 nm of silica was activated by Brown treatment, that is to say dipped in a 0.1N sodium hydroxide bath.

Silica particles with a mean diameter of 1 μm were functionalized with a 5 mM solution of 5,6-epoxyhexyltriethoxysilane in toluene at 80° C. for 16 hours. The substrate was rinsed with distilled water and then annealed by drying at 110° C. for 3 hours.

The functionalized particles were deposited on a surface of the substrate by the Langmuir-Blodgett method at a draw rate of 1 cm/min.

This first layer of particles was subsequently heat treated at 110° C. for 3 hours in order to anchor this layer to the substrate by establishment of covalent bonds, as in example 1.

Subsequently, 50 layers of particles identical to those deposited for the first layer were deposited by the Langmuir-Blodgett method at a draw rate of 1 cm/min.

REFERENCES

[1] Somobrata Acharya, Jonathan P. Hill and Katsuhiko Ariga, "Soft Langmuir-Blodgett Technique for Hard Nanomaterials", Adv. Mater., 2009, 21, 2959-2981.
[2] Maria Bardosova, Martyn E. Pemble, Ian M. Povey and Richard H. Tredgold, "The Langmuir-Blodgett Approach to Making Colloidal Photonic Crystals from Silica Spheres", Adv. Mater., 2010, 22, 3104-3124.
[3] Masahiro Shishido and Daisuke Kitagawa, "Preparation of ordered mono-particulate film from colloidal solutions on the surface of water and continuous transcription of film to substrate", Colloids and Surfaces A: Physiochem. Eng. Aspects, 311 (2007), 32-41.
[4] Sanjib Biswas and Lawrence T. Drzal, "A Novel Approach to Create a Highly Ordered Monolayer Film of Graphene Nanosheets at the Liquid-Liquid Interface", Nano Left., Vol. 9, No. 1, 2009.
[5] Feng Pan, Junying Zhang, Chao Cai and Tianmin Wang, "Rapid Fabrication of Large-Area Colloidal Crystal Monolayers by a Vortical Surface Method", Langmuir, 2006, Vol. 22, No. 17, pp 7101-7104.
[6] Y. J. Zhang, W. Li and K. J. Chen, "Application of two-dimensional polystyrene arrays in the fabrication of ordered silicon pillars", Journal of Alloys and Compounds, 450 (2008), 512-516.
[7] J. Rybczynski, U. Ebels and M. Giersig, "Large-scale, 2D arrays of magnetic nanoparticles", Colloids and Surfaces A: Physicochem. Eng. Aspects, 219 (2003), 1-6.
[8] D. Nagao, R. Kameyama and H. Matsumoto, "Single- and multi-layered patterns of polystyrene and silica particles assembled with a simple dip-coating", Colloid and Surfaces A: Physiochem. Eng. Aspects, 2008, Vol. 317, pp 722-729.
[9] S. Rakers, L. F. Chi and H. Fuchs, "Influence of the Evaporation Rate on the Packing Order of Polydisperse Latex Monofilms", Langmuir, 1997, 13, 7121-7124.
[10] V. Conedera, N. Fabre and H. Camon "Les matériaux élaborés par sol-gel et leur utilisation en micro Technologies [Materials prepared by the sol-gel process and their use in microtechnologies]", LAAS Report No. 02217 (2002).
[11] P. Coudray, P. Etienne and Y. Moreau, "Integrated optics based on organo-mineral materials", Invited paper of European materials conference-Strasbourg (1999).
[12] R. C. Liang, M. Chan-Park, S. C-J, Tseng, Z-A G. Wu and H. M. Zang, "Electrophoretic display", Patent Publication No. WO 01/67171 A1, (2001).
[13] R. C. Liang, Z-A. G. Wu and H. M. Zang, "Manufacturing process for multi-layer color displays", Patent Publication No. WO2004/051353 (2004).
[14] T. Ozawa, S. Ishiwata and Y. Kano, "Adhesive Properties of Ultraviolet Curable Pressure-Sensitive Adhesive Tape for Semiconductor Processing (I)-Interpretation via Rheological Viewpoint", Furukawa Review, 20, 83 (2001).

The invention claimed is:

1. A process for the manufacture of a chromatography analytical column of the open tube having a porous layer type, characterized in that it comprises the following steps:
   a) deposition of a first layer (2) of identical or different particles, which are intended to form the stationary layer, on the flat surface of a substrate (1),
   b) deposition of at least one second layer (12) of particles as a compact assemblage on the layer (2),
   c) impregnation of the layers (2, 12) with a material sensitive to light radiation (4), in order to form at least two layers (3) of particles as a compact assemblage impregnated with sensitive materials,
   d) insolation of the layers (3) in the regions corresponding to the internal shape desired for the chromatography analytical column, when the material sensitive to light radiation (4) behaves as a positive resin, or outlining this internal shape, when the material sensitive to light radiation (4) behaves as a negative photosensitive resin,
   e) removal:
      of the regions insolated in step d), when the material sensitive to light radiation (4) behaves as a positive photosensitive resin, or
      of the regions not insolated in step d), when the material sensitive to light radiation (4) behaves as a negative photosensitive resin, and f) covering and sealing the structure obtained in step e) with a covering cap (7) covered, on its face turned towards the layers (3), with at least one layer of particles as a compact assemblage identical to or different from those deposited on the surface of the substrate (1).

2. The process as claimed in claim 1, characterized in that it additionally comprises, before step a), a step a1) of activation of said surface of the substrate (1), preferably by O2 plasma, UV radiation, a mixture of sulfuric acid and of hydrogen peroxide, or ozone.

3. The process as claimed in claim 2, characterized in that it additionally comprises, after step a1) of activation of said surface of the substrate (1), a step a2) of thermal annealing of said surface of the substrate (1) which has been subjected to step a1).

4. The process as claimed in claim 1, characterized in that it additionally comprises, after step c) of impregnation of the layers (2), a step c1) of thermal annealing of the substrate (1) and of the layers (3).

5. The process as claimed in claim 1, characterized in that it additionally comprises, after step d) of insolation of the layers (3), a step d1) of thermal annealing of the substrate (1) coated with the insolated layers (3).

6. The process as claimed in claim 1, characterized in that it additionally comprises, after step e) of removal of the insolated or non-insolated regions, a step e1) of annealing of the substrate (1) covered with the layers (3), certain regions of which have been removed.

7. The process as claimed in claim 1, characterized in that it additionally comprises a step of formation of at least one layer of particles as a compact assemblage on a face of the covering cap (7).

8. The process as claimed in claim 1, characterized in that said particles have a mean diameter of between 50 nm and 500 μm inclusive.

9. The process as claimed in claim 1, characterized in that the total thickness of the layers (2, 12) is between 50 and 700 μm inclusive.

10. The process as claimed in claim 1, characterized in that the particles are particles made of a metal oxide, or made of a ceramic, or made of a polymer, or made of a polysaccharide, or made of a metal; these particles optionally being functionalized.

11. The process as claimed in claim 1, characterized in that step a) is carried out by the Langmuir-Blodgett method, or by the Langmuir-Schaefer method, or by Marangoni self-assembling, or by the vortical surface method, or by floating-transferring, or by dip coating, or by spin coating.

12. The process as claimed in claim 1, characterized in that the material sensitive to light radiation (4) behaves as a positive resin and is sensitive to radiation with wavelengths of between 150 and 700 nm inclusive.

13. The process as claimed in claim 1, characterized in that the material sensitive to light radiation (4) behaves as a negative resin and is sensitive to radiation with wavelengths of between 150 and 700 nm inclusive.

14. The process as claimed in claim 1, characterized in that the material sensitive to light radiation (4) is obtained by a sol-gel process.

15. The process as claimed in claim 1, characterized in that step c) is carried out by spin deposition of the material sensitive to light radiation (4) on the layer (2) or by immersion of the substrate (1) coated with the layer (2) in the material sensitive to light radiation (4).

16. The process as claimed in claim 1, characterized in that step d) of insolation of the layers (3) with the light radiation (4) is carried out through a mask (11) comprising regions transparent to said light radiation (4), these transparent regions corresponding to:
the internal shape desired for the chromatography analytical column, when the material sensitive to light radiation (4) behaves as a positive resin, or
outlining this internal shape, when the material sensitive to light radiation (4) behaves as a negative resin.

17. The process as claimed in claim 1, characterized in that step d) of insolation of the layers (3) is carried out by laser writing in order to form the internal shape desired for the column, when the material sensitive to light radiation (4) behaves as a positive resin, or in the regions outlining this internal shape, when the material sensitive to light radiation (4) behaves as a negative resin.

18. The process as claimed in claim 1, characterized in that the substrate is rigid or flexible and made of a material chosen from a metal oxide, a metal, a ceramic or a polymer.

19. The process as claimed in claim 1, characterized in that the particles are made of a material chosen from silica, titanium dioxide, alumina, latex, polydimethylsiloxane (PDMS), gold, copper and the mixtures of these.

20. A chromatography analytical column, characterized in that it comprises a substrate (1), a flat surface of which is coated with at least one layer (3) of particles, this layer (3) of particles, which are optionally functionalized, comprising a region (5) devoid of the particles and forming the internal portion of the column and in that at least one wall of the column consists of a mixture of said particles, which are optionally functionalized, and of a material sensitive to light radiation, which is crosslinked.

21. The column as claimed in claim 20, characterized in that the particles are particles made of a metal oxide, polymer, polysaccharide, metal or ceramic, these particles optionally being functionalized.

22. The column as claimed in claim 20, characterized in that the particles have a mean diameter of between 50 nm and 500 μm inclusive.

23. The column as claimed in claim 20, characterized in that the substrate (1) is flexible or rigid and is made of a material chosen from a metal oxide, a metal, a ceramic or a polymer.

24. The column as claimed in claim 20, characterized in that the particles are made of a material chosen from silica, alumina, titanium oxide, latex, polydimethylsiloxane (PDMS), gold, copper or mixtures of these.

* * * * *